United States Patent [19]
Weber et al.

[11] Patent Number: 6,054,599
[45] Date of Patent: Apr. 25, 2000

[54] PHYTOSPHINGOSINE-BASED CERAMIDE I ANALOGS

[75] Inventors: Pieter Gijsbert Weber, Ridderkerk; Johannes Wilhelmus Jacobus Lambers, Pijnacker; Hein Simon Koger, Spaarndam; Jan Verweij, Leiden, all of Netherlands

[73] Assignee: DSM N.V., Netherlands

[21] Appl. No.: 09/072,808

[22] Filed: May 5, 1998

Related U.S. Application Data

[63] Continuation of application No. 08/649,678, filed as application No. PCT/EP94/03592, Oct. 28, 1994, Pat. No. 5,919,960.

[30] Foreign Application Priority Data

Oct. 28, 1993 [EP] European Pat. Off. .............. 93203016
Oct. 29, 1993 [EP] European Pat. Off. .............. 93203041
Sep. 6, 1994 [EP] European Pat. Off. .............. 94202550

[51] Int. Cl.$^7$ ................................................ C07C 233/00
[52] U.S. Cl. ................................ 554/66; 554/69; 554/63; 514/613; 514/627; 514/861; 514/873
[58] Field of Search ............................... 554/103, 66, 64; 514/613, 627, 861, 873

[56] References Cited

U.S. PATENT DOCUMENTS 5,627,056  5/1997  Casey et al. .

FOREIGN PATENT DOCUMENTS 0 373 038 A2  12/1988  European Pat. Off. .
0 398 272 A1  11/1990  European Pat. Off. .
0 455 429 A2  11/1991  European Pat. Off. .
0 482 860 A1   4/1992  European Pat. Off. .
   94/10131    5/1994  WIPO .......................... C07C 235/08
WO 94/10131   5/1994  WIPO .

OTHER PUBLICATIONS

Motta, S., et al., "Ceramide Composition of the Psoriatic Scale" *Biochem Biophys Acta* (1993) 1182(2):147–151.

*Primary Examiner*—Deborah Carr
*Attorney, Agent, or Firm*—Morrison & Foerster LLP

[57] ABSTRACT

Novel phytosphingosine-based analogs of ceramide I, methods for the preparation of these novel compounds, cosmetic and pharmaceutical compositions containing such compounds, and methods for the use thereof are described.

14 Claims, No Drawings

PHYTOSPHINGOSINE-BASED CERAMIDE I ANALOGS

The present application is a continuation of U.S. Ser. No. 08/649,678, filed Apr. 29, 1996, now U.S. Pat. No. 5,919,960 which itself represents the United States national phase of PCT/EP94/03592, internationally filed on Oct. 28, 1994. The complete text of the '678 application, and the international specification including any amendments thereto as accepted by the IPEA/EP, are incorporated by reference herein as if fully set forth.

The present invention relates to novel compounds related to natural ceramide I for use in cosmetic and pharmaceutical formulations.

BACKGROUND OF THE INVENTION

Ceramides are the main lipid component in the upper layer of the skin, the stratum corneum. The stratum corneum has an important barrier function: external compounds are generally kept outside and the loss of moisture is limited.

The addition of ceramides to skin cosmetic products improves the barrier function of the skin, restores lost moisture and has been found to have "anti-wrinkle" effects. Moreover, ceramides have also found use in pharmaceutical preparations for example for the treatment of atopic eczema (Kerscher et al. (1991) Eur. J. Dermatol., 1, 39–43). European Patent Application EP 0 373 038 describes the therapeutic use of N-acyllysosphingolipids, wherein the acyl group has a chain length of 2–24 carbon atoms and is substituted by one or more polar groups.

In particular, ceramide I, described in European Patent 0 097 059 (Unilever/Conopco) is commonly found in commercial cosmetic preparations. The structure of ceramide I was investigated by Wertz et al. ((1985) J. Invest. Dermatol., 84(8), 410–412—see also Wertz and Downing (1983) J. Lipid Res., 24, 759–765; Wertz et al. (1983) Biochim. Biophys. Acta, 753, 350–355; Kerscher et al. (1991); supra, p. 41) and is depicted below:

human stratum corneum, Motta et al., Biochimica et Biophysica Acta, 1182, pp. 147–151 1993).

However, it has also been found that sphingosine-based ceramides such as natural ceramide I are broken down in the skin by the action of ceramidases to liberate sphingosine. Free sphingosine inhibits the activity of protein kinase C and in this way may affect cell division. It has been proposed that the effects of free sphingosine may be an important factor in the modulation of epidermal cell proliferation in order to balance the rate in which cells are lost from the skin surface (Downing, D. T. (1992) J. Lipid Res., 33, 301–313).

Nevertheless, as mentioned above, natural ceramide I is commonly found in cosmetic preparations containing ceramides. Thus, the application of ceramide I-containing cosmetics to the skin may lead to the accumulation of an excess of free sphingosine due to the subsequent action of the ceramidases endogenous to the statum corneum. As a result, the fine balance of epidermal cell modulation may be upset.

On the other hand, the presence of phytosphingosine could not been demonstrated in the skin, despite efforts to locate it (Wertz and Downing (1990) J. Invest. Dermatol., 94(2), 159–161; Wertz and Downing (1989) Biochim. Biophys. Acta, 1002(2), 213–217). This may indicate that the ceramidases which degrade sphingosine-based ceramides are not active on phytosphingosine-based ceramides.

Another drawback of the use of natural ceramide I in cosmetics is that this ceramide is difficult to obtain in a cost-effective way in the quantities needed for application in cosmetic preparations. Isolation from natural sources is laborious and expensive, resulting in only small amounts of pure ceramide I. A solution to this problem may be the chemical synthesis of ceramide I from its constituents sphingosine and an acyloxyalkanoic acid. However, this is not a very realistic option, because the sphingosine constituent is not easily obtainable in the amounts necessary for larger scale synthesis reactions.

Accordingly, it would be desirable to develop analogs of natural ceramide I which would maintain their efficacy as (Formula 1)

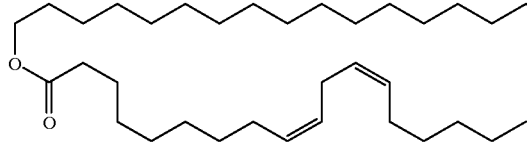
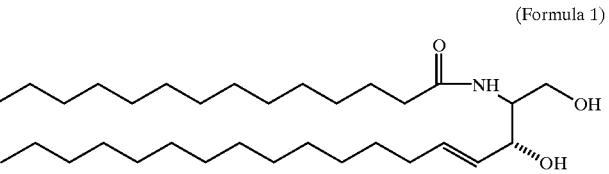

Several references postulate that ceramide I has a unique function in relation to other known ceramides. It appears that ceramide I, with its characteristic acyl-ceramide structure, acts as a sort of "molecular rivet" whereby the extracellular lipid bilayers of the stratum corneum are bound to one another, thus maintaining the skin's characteristic barrier function (permeability-regulating) and its moisture-retaining properties (see Melton et al. (1987) Biochim. Biophys. Acta, 921(2), 191–197; Wertz and Downing (1988) Lipids, 23(5), 415–418; Brooks and Idsen (1991) Int. J. Cosmet. Sci., 13, 103–113; Wertz et al. (1983) Biochim. Biophys. Acta, 753, 350–355; and Kerscher et al. (1991) supra). The analysis of the ceramide composition in the skin disorder psoriasis, a skin disorder which is characterized by an impaired barrier function, showed a significantly decreased content of ceramide I, as compared to normal "molecular rivets" of the extracellular lipid bilayers of the stratum corneum, thus maintaining and enhancing the skin's barrier and moisture-retaining functions without upsetting the balance of epidermal cell modulation which could result from an excess of sphingosine in the epidermis. In addition, it would be most desirable to obtain such analogs of natural ceramide I in a cost-effective way.

SUMMARY OF THE INVENTION

The present invention provides phytosphingosine-based analogues of ceramide I wherein the sphingosine backbone of ceramide I is replaced by a phytosphingosine backbone.

The present invention further provides methods for the preparation of the novel phytosphingosine-containing ceramide I analogues. Also disclosed are methods for the preparation of acyloxy-alkanoic acids and ω-hydroxy alkanoic acids.

The compounds of the present invention are used in pharmaceuticals. In addition, the compounds of the present invention are used in cosmetics.

The present invention provides cosmetic and pharmaceutical preparations for topical application which restore and enhance the skin's barrier and moisture-retaining functions.

The compounds of the present invention may be present in the compositions of the present invention in a range of from 0.001% to 25% in such cosmetic and pharmaceutical formulations. Preferably the compounds of the present invention are present in the range of 0.005% to 5%, more preferably 0.02% to 2% and most preferably about 0.5%.

DETAILED DESCRIPTION OF THE INVENTION

The present invention describes novel analogs of ceramide I wherein the sphingosine backbone of the natural compound is replaced by a phytosphingosine backbone.

The novel compounds of the present invention have the general formula:

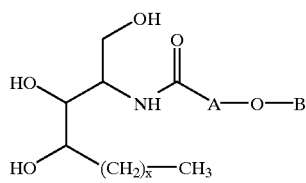

(Formula 2)

wherein A is a $C_{10}$ or greater straight chain alkyl group which may optionally contain one or two double bonds and B is a hydrogen atom or a $C_{5-25}$ straight chain acyl group which may optionally contain one or two double bonds. X is an integer from 10–25, inclusive.

Preferred compounds of the present invention are those wherein A is a $C_{15-35}$, straight chain alkyl group which may optionally contain one or two double bonds, more preferably a $C_{22-31}$ group which may optionally contain one or two double bonds and B is a $C_{12-20}$ straight chain acyl group which may optionally contain one or two double bonds and even more preferred wherein B is stearoyl, oleoyl or lineoyl. Examples of such compounds are N-(27-stearoyloxy-heptacosanoyl)-phytosphingosine, N-(27-lineoyloxy-heptacosanoyl)-phytosphingosine, N-(27-oleoyloxy-heptacosanoyl)-phytosphingosine, N-(23-stearoyloxy-tricosanoyl)-phytosphingosine, N-(23-lineoyloxy-tricosanoyl)-phytosphingosine, N-(23-oleoyloxy-tricosanoyl)-phytosphingosine. Most preferred compounds are those wherein A is as defined above and B is lineoyl.

It should also be understood that the value of X in the phytosphingosine moiety, is preferably 13, but is intended to include analogs wherein the saturated alkyl chain tail, which extends from the 4-OH position, is from 11 to 26 carbons in total length (i.e. X is 10–25), such as is described by Wertz et al. ((1985) supra, p. 411).

The phytosphingosine-based ceramide I analogs may be prepared by various chemical synthesis methods known to the skilled artisan such as the selective acylation method of Smeets and Weber (WO 93/20038) or a method analogous to that of Mori and Nishio (1991) Liebigs Ann. Chem., 253–257. The choice of the synthesis method is not critical to the present invention.

The compounds of the present invention may be prepared via an amidation reaction of a straight chain acyloxy-alkanoic acid of the general formula:

(Formula 3)

B—O—A—COOH wherein A and B are as previously defined, with phytosphingosine.

The coupling between either an acyloxy-alkanoic acid or an ω-hydroxy alkanoic acid and phytosphingosine can be carried out either enzymatically or chemically.

Numerous methods are available to a person skilled in the art for the chemical coupling between either an acyloxy-alkanoic or an ω-hydroxy alkanoic acid and phytosphingosine. These include methods wherein the acid can be coupled either as such using coupling reagents, e.g. EEDQ (N-ethoxycarbonyl-2-ethoxy-1,2-dihydroquinoline) and/or HOBT (hydroxybenzotriazole), or N-hydroxysuccinimide, or a carbodiimide, or as an activated acid e.g. a mixed anhydride or acid halogenide.

A preferred chemical synthesis method using a mixed anhydride in the coupling reaction, is the selective acylation method published by Smeets and Weber (supra). The coupling reaction is performed via a two-step method, the first step comprising the formation of a mixed anhydride via the reaction of a saturated straight chain acyloxy-alkanoic acid (Formula 3), or a salt thereof, with a sulfonyl chloride in organic solvent and in the presence of an organic base, followed by a second step wherein the mixed anhydride formed in the first step is reacted with phytosphingosine. Both steps may be optionally performed in a single reaction vessel ("one-pot process").

Phytosphingosine is obtainable efficiently by deacetylation of tetra-acetylphytosphingosine (TAPS). The deacetylation may be chemical, e.g. by base catalyzed hydrolysis with potassium hydroxide, or enzymatical. After alkaline hydrolysis of TAPS, the resulting phytosphingosine may be purified according to any method known to a person skilled in the art.

TAPS is obtainable efficiently in large amounts by microbial fermentation, especially by fermentation of Hansenula, more especially by fermentation of *Hansenula ciferrii*.

The acyloxy-alkanoic acid of Formula 3 may be prepared by standard techniques known to the skilled artisan, such as a method analogous to that described by. Mori and Nishio (supra) or a manner analogous to that described by Heslinga and Pabon (1984) Recl. Trav. Chim. Pays-Bas, 103, 348–351. Again the choice of the synthesis method is not critical to the present invention.

Preferably, the compounds of Formula 3 may be prepared by reacting an ω-hydroxy alkanoic acid ($C_{10}$ or longer) with a selected $C_{5-25}$ (optionally unsaturated) straight chain fatty acid wherein the acid moiety of the former starting material is preferably protected with a protecting group known to those skilled in the art. Suitable protecting groups are described in Greene, T. (1981) *Protective Groups in Organic Synthesis* (John Wiley & Sons; New York). For instance, silyl, allyl, t-butyl, benzyl can be used. It has to be kept in mind that the reagents and/or solvents as well as the reaction conditions should be chosen in such a way that they do not interfere with the protecting group and that the addition as well as the removal of the protecting group should not destroy the starting material or the compound to be synthesized.

The ω-hydroxy alkanoic acids may be obtained from carnauba wax (Wertz et al. (1985), supra) or may be synthesized chemically by methods well within the knowledge of the skilled artisan such as a method analogous to that described by Schill, G. (1966) Chem. Ber., 99, 2689–2698.

The present invention describes a novel and simple method to obtain various ω-hydroxy acids with different chain length, via the coupling of protected acid chlorides of variable chain length with enamines prepared from cyclic ketones of variable size, followed by ring opening and reduction. In this way, the ω-hydroxy alkanoic acid can be provided with any chain length that is desirable.

In another embodiment, ω-hydroxy alkanoic acids may be obtained by hydrolysis of a cyclic lactone.

The novel ceramide I analogs of the present invention have several advantages above natural ceramide I. The ceramide I analogs may be less susceptible to degradation by the ceramidases endogenous to the stratum corneum and, importantly, they are obtainable in a more cost-effective way. In addition, they have a higher oxidation stability, since the ceramide I analogs of the present invention lack the double bond which is present in the sphingosine moiety of natural ceramide I. Thus, the ceramide I analogs of the present invention may be applied beneficially in cosmetic and pharmaceutical preparations for topical use on the skin.

Once obtained, the compounds of the present invention may be formulated in oil/water or water/oil compositions suitable for cosmetic or pharmaceutical use.

In addition to the compounds of the present invention, which serve as the active ingredients in the cosmetic and pharmaceutical compositions of the present invention, other cosmetically and pharmaceutically excipients may be employed including diluents, dispersants, solvents, emollients. Perfume may also be optionally employed. Such vehicles are well-known to those skilled in the art and are described in detail in the literature, for example, in European Patent No. 0 097 059 which is incorporated herein by reference.

The compounds of the present invention may be present in the compositions of the present invention in a range of from 0.001% to 25% in such cosmetic and pharmaceutical formulations. Preferably the compounds of the present invention are present in the range of 0.005% to 5%, more preferably 0.02% to 2% and most preferably about 0.5%.

The compositions of the present invention may optionally contain more than one of the herein described phytosphingosine-based ceramide I analogs.

The cosmetic and pharmaceutical compositions of the present invention may be applied topically to mammalian skin and are useful, inter alia, in restoring moisture to the skin and in the treatment of atopic eczema.

EXAMPLE 1

The Synthesis of N-(27-stearoyloxy-heptacosanoyl)-phytosphingosine

A. The Synthesis of 15-hydroxy-pentadecanoic acid.

To a solution of cyclopentadecanolide (300.5 g; 1.25 mole) in ethanol (1500 ml) a solution of sodium hydroxide (65

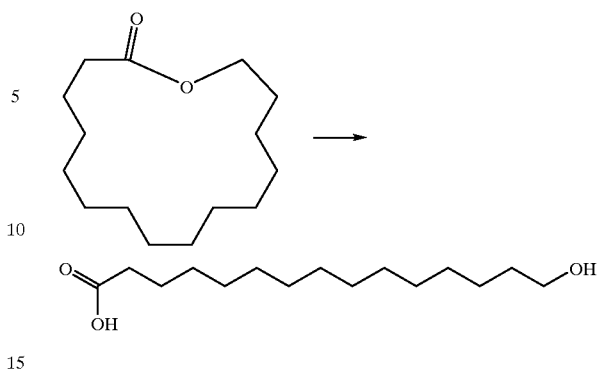

g; 1.625 mole) in water (400 ml) was added at 40° C. After refluxing under nitrogen for 90 minutes the reaction mixture was cooled down to 70° C. and poured into a stirred mixture of water (3 l) and hydrochloric acid (36%; 150 ml). After filtration the precipitate was filtered off, washed subsequently with a mixture of ethanol and water (600 ml; v/v=1:2) and water (2×1 l) and dried in vacuo giving 318.2 g of the title product.

PMR-spectrum (Bruker; 360 MHz; CDCl$_3$/DMSO-d6 v/v 1:1); values in ppm; δ DMSO 2.5). δ: 1.1–1.6 (m, 24H); 2.14 (t, 2H); 3.40 (t, 2H).

B. The Synthesis of 15-acetoxy-pentadecanoylchloride.

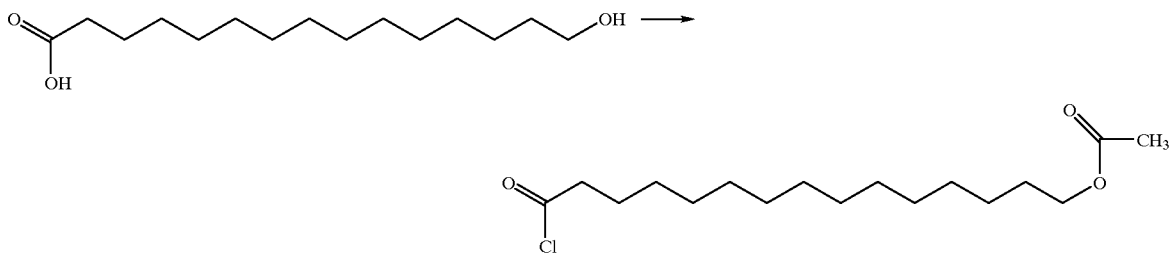

A mixture of 15-hydroxypentadecanoic acid (387 mmoles) and acetyl chloride (250 ml) was stirred at room temperature. When evolution of hydrochloric acid ceased first 100 g (387 mmoles) of 15-hydroxypentadecanoic acid was added and then another 118 g (457 mmoles) of the acid together with 50 ml of acetyl chloride. The reaction mixture was heated and distillation was started until the reaction temperature was 130° C. The reaction mixture was cooled down till 35° C. and thionyl chloride (300 ml) was added. After refluxing gently for 150 minutes the excess of thionyl chloride was distilled off and the residue was distilled in vacuo. The fraction that was obtained at 203–218° C./1–5 mm Hg appeared to be the title compound and was used as such in subsequent reactions.

PMR-spectrum (Bruker; 360 MHz; CDCl$_3$); values in ppm; δ CDCl$_3$ 7.27 ppm. δ: 1.2 (broad s, 20H); 1.6 (m, 4H); 1.98 (s, 3H); 2.83 (t, 2H); 3.99 (t, 2H).

C. The Synthesis of 1-morpholino-cyclododecene.

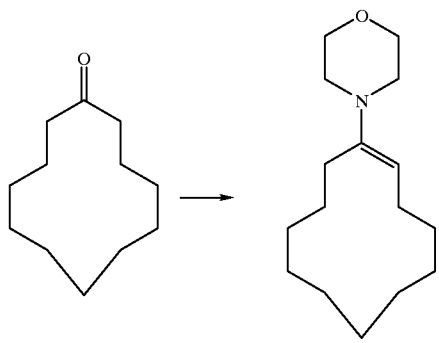

A mixture of cyclododecanone (500 g; 2.74 mole), toluene (1000 ml), morpholine (332 g; 3.82 mole) and p-toluenesulphonic acid monohydrate (7.5 g) was refluxed with stirring for 96 hours using a Dean Stark apparatus in which 75 ml of water was separated. After concentrating in vacuo the reaction mixture was distilled using a condenser initially without and then with water. The title product (386.2 g) was obtained at 176–198° C. at 0,5 mm Hg.

PMR-spectrum (Bruker; 360 MHz; $CDCl_3$); values in ppm; δ tetra-methyl silane: 0 ppm. δ: 1.1–1.5 (m, 16H); 2.09 (q, 2H); 2.22 (t, 2H); 2.75 (m, 4H); 3.71 (m, 4H); 4.36 (t, 1H).

D. The Synthesis of 27-hydroxy-heptacosanoic acid.

15-Acetoxy-pentadecanoyl chloride (151 g; 0.47 mole) was added to a stirred mixture of 1-morpholino-cyclododecene (133 g; 0.53 mole) and chloroform (500 ml, free of alcohol) under nitrogen during 35 minutes. The temperature raised to 46° C. After stirring for 2 hours a mixture of 82 ml of water and 125 ml of hydrochloric acid (36%) was added and this mixture was refluxed for 4 hours at 62° C. After cooling the flask to room temperature the layers were separated and the organic

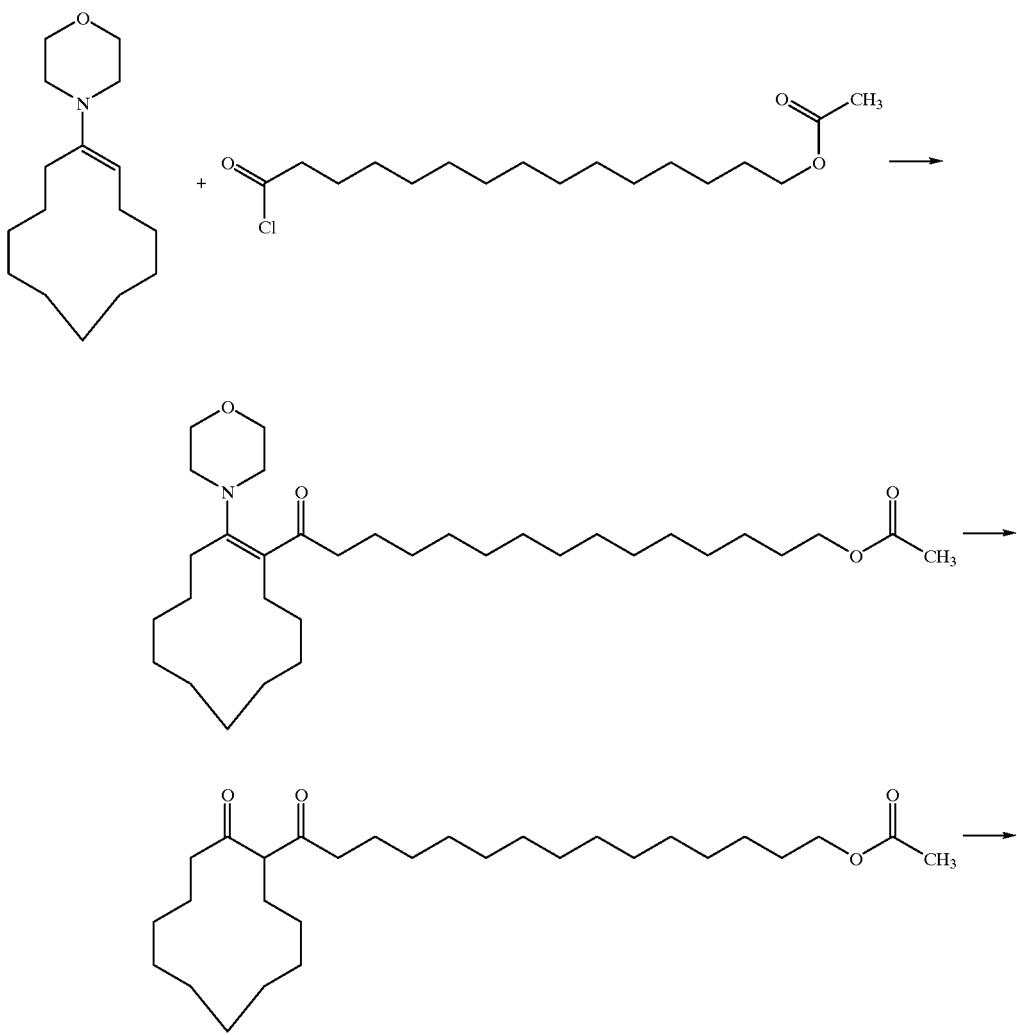

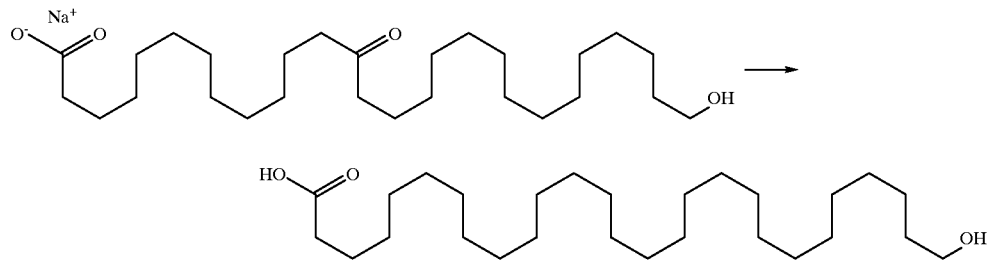

layer was washed with 250 ml of iN hydrochloric acid. The water layer was extracted with 100 ml of chloroform. The combined chloroform layers were concentrated giving 240 g of crude (15-acetoxy-pentadecanoyl)-cyclododecanone.

PMR-spectrum (Bruker; 360 MHz; CDCl$_3$); values in ppm; δ CHCl$_3$ 7.27 ppm). δ: 1.0–1.8 (m, 42H); 2.01 (s, 3H); 2.4 (m, 4H); 3.58 (t, 1H); 4.02 (t, 2H).

Subsequently a mixture of crude (15-acetoxy-pentadecanoyl)-cyclododecanone (190 g; about 0.37 mole), diethylene glycol (400 ml), absolute ethanol (200 ml) and sodium hydroxide (80 g) was heated with stirring under nitrogen at 98° C. for 1 hour and distilled till the temperature raised to 122° C. After addition of 200 ml of diethylene glycol hydrazine hydrate (120 ml) was added and heating was continued for 2 hours at 123° C. Then the mixture was distilled until 180 ml of liquid was collected, while the temperature raised to ca 220° C. After the mixture was heated for 2 hours at 225° C. it was cooled to about 180° C., poured out into a mixture of 2000 ml of water and 200 ml of hydrochloric acid (36%) and filtered while still warm (50° C.). After being washed with water (2×250 ml) the wet filter cake was heated with 1 l of toluene. The layers were separated and the toluene layer was concentrated under atmospheric pressure (200 ml was distilled off) and cooled to room temperature. The crystalline title product (120 g) was obtained by filtration, washing with toluene (100 ml) and hexane (150 ml) and drying.

PMR-spectrum (Bruker; 360 MHz; CDCl$_3$/DMSO-d6 v/v 1:1); values in ppm; δ DMSO 2.5 ppm). δ: 1.1–1.5 (m, 48H); 2.13 (t, 2H); 3.41 (t, 2H).

E. The Synthesis of Benzyl 27-hydroxyheptacosanoate.

A suspension of 27-hydroxyheptacosanoic acid (100 g; 234 mmoles) in a mixture of dimethylformamide (500 ml), acetone (500 ml), benzyl bromide (50 ml) and dry potassium carbonate (50 g) was refluxed with stirring for 3 hours at about 76° C. After adding 10 ml of benzyl bromide refluxing was continued for 1 hour, another 10 ml of benzyl bromide was added. Refluxing was still continued for 1 hour and then the mixture was cooled to 50° C. and poured out into 2 l of water with vigorous stirring. The precipitate was filtered off and washed with water (3×: 1000 ml; 500 ml; 500 ml). The wet filter cake was heated with 1 l of toluene. The layers were separated in a preheated separation funnel. The water layer was extracted with 100 ml warm toluene. The combined toluene layers were concentrated under atmospheric pressure (200 ml was distilled off) and cooled slowly to 21° C. The crystalline title product (76.6 g) was obtained by filtration, washing with toluene (200 ml) and drying in vacuo.

PMR-spectrum (Bruker; 360 MHz; CDCl$_3$/CD$_3$OD); values in ppm; δ CD$_3$OD 3.35 ppm). δ: 1.2–1.7 (m, 48H); 2.36 (t, 2H); 3.57 (t, 2H); 5.12 (s, 2H); 7.3 (m, 5H).

F. The Synthesis of Benzyl 27-stearoyloxyheptacosanoate.

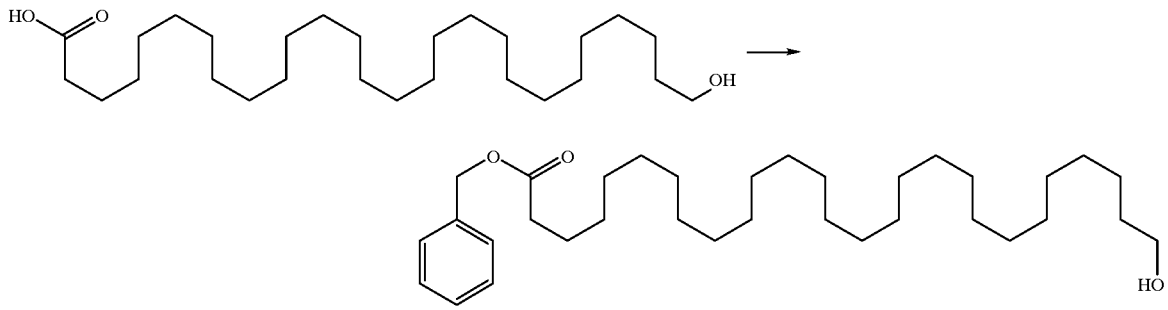

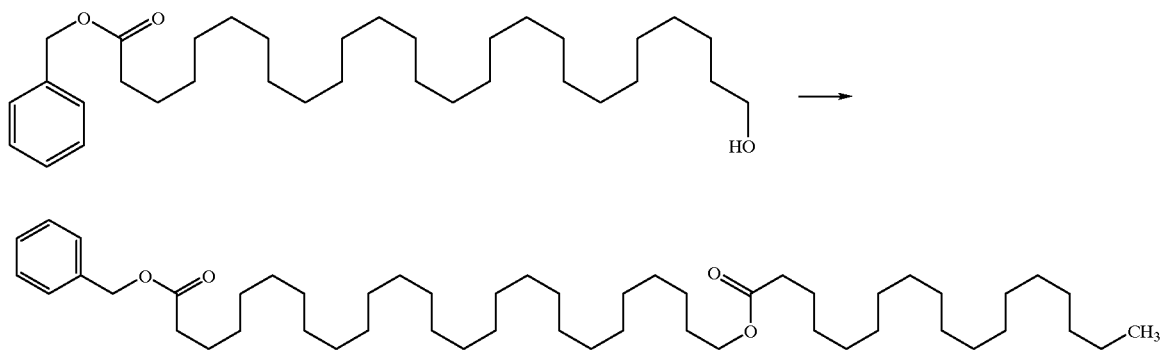

Stearoyl chloride (75 ml) was added to a mixture of benzyl 27-hydroxyheptacosanoate (100 g; 193 mmoles) and pyridine (775 ml). After stirring for 150 minutes another 10 ml of stearoyl chloride was added, and stirring was continued for 23 hours. After careful addition of 75 ml of water and stirring for 24 hours the precipitate formed was filtered off, washed subsequently with pyridine-water (v/v: 90/10), water (5×250 ml) and methanol (400 ml). Drying in vacuo afforded 124.3 g of the title product.

PMR-spectrum (Bruker; 360 MHz; $CDCl_3$); values in ppm; δ $CHCl_3$ 7.27 ppm). δ: 0.89 (t, 3H); 1.2–1.7 (m, 78H); 2.29 (t, 2H) ; 2.36 (t, 2H); 4.06 (t, 2H); 5.12 (s, 2H); 7.3 (m, 5H).

G. The Synthesis of 27-stearoyloxyheptacosanoic acid.

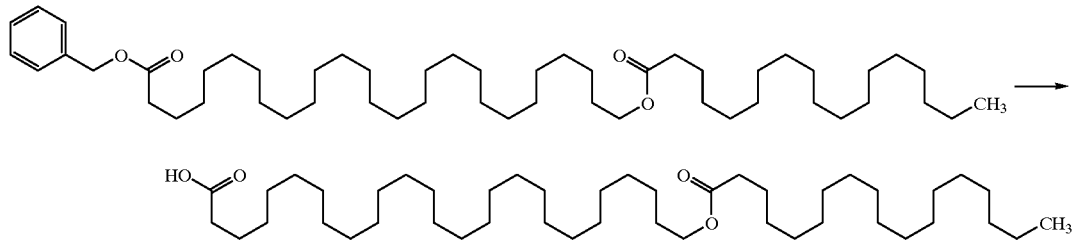

Palladium on activated carbon (10 g; 10%) was added to a solution of benzyl 27-stearoyloxyheptacosanoate (132 g; 168 mmoles) in methylene chloride (350 ml; free of alcohol) at 30° C. After purging with nitrogen hydrogen was led over the mixture with stirring for 2 hours and the reaction mixture was then again purged with nitrogen. After concentrating the reaction mixture in vacuo chloroform (500 ml; free of alcohol) was added and the palladium catalyst was filtered off. The filtrate was washed again and concentrated in vacuo. The residu was recrystallised with 600 ml warm toluene giving 104.6 g of the title product.

PMR-spectrum (Bruker; 360 MHz; $CDCl_3$pyridine-d5; v/v: 1/1); values in ppm; δ $CHCl_3$ 8.11 ppm). δ: 0.87 (t, 3H); 1.0–1.7 (m, 78H); 2.30 (t, 2H); 2.32 (t, 2H); 4.07 (t, 2H).

H. The Synthesis of N-(27-stearoyloxyheptacosanoyl)-phytosphinaosine.

A. Via a Mixed Anhydride p-Toluenesulphonic acid (13.55 g; 71.1 mmoles) was added to a refluxing solution of 27-stearoyloxyheptacosanoic acid (53.45 g; about 77.1 mmoles) and triethylamine (100 ml) in methylene chloride (2 l; free of alcohol) under nitrogen. After refluxing for 1 hour phytosphingosine (18.6 g; purity 94%; 55 mmoles) was added and refluxing was continued for 145 minutes. After cooling the reaction mixture to 30° C. the precipitate was filtered off and washed with methylene chloride (1 l). This solid was dissolved in hot, ethanol-free

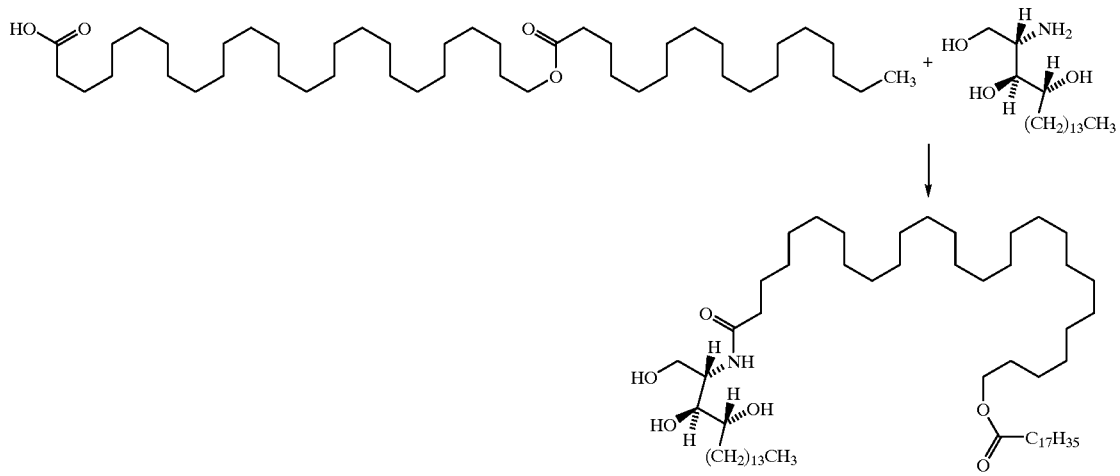

chloroform and filtered off while warm. The filtrate was allowed to cool. The precipitate formed was filtered off, washed with chloroform (250 ml) and acetone (2×200 ml) and dried in vacuo affording 41 g of the title product.

PMR-spectrum (Bruker; 360 MHz; CDCl$_3$/pyridine-d5; v/v: 1/1); values in ppm; 328° K.; CHCl$_3$ 7.81 ppm). δ: 0.93 (t, 6H); 1.0–2.0 (m, 110H); 2.27 (t, 2H); 2.35 (t, 2H); 3.8–4.4 (m, 6H); 4.58 (m, 1H); 5.53, 5.66 and 6.16 (3×broad s; 3×1H).

B. Using a Carbodiimide

A mixture of 27-stearoyloxyheptacosanoic acid (8.88 g, 12.8 mmoles), tetrahydrofuran (120 ml), dried 1-hydroxybenzotriazole (4 g, 34.1 mmoles), phytosphingosine (3.91 g, 12.33 mmoles) and N,N'-diisopropylcarbodiimide (2.55 ml, 16.3 mmoles) was stirred under nitrogen for 2 hours at 40° C. and for another 4 hours at 50° C. After filtration and recrystallisation from hot chloroform 8.84 g of the title compound was obtained.

EXAMPLE 2

The Synthesis of N-(27-linoleoyloxyheptacosanoyl)-phytosphingosine

A. The Preparation of 27-linoleoyloxyheptacosanoic acid.

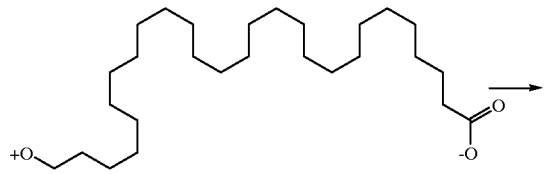

-continued

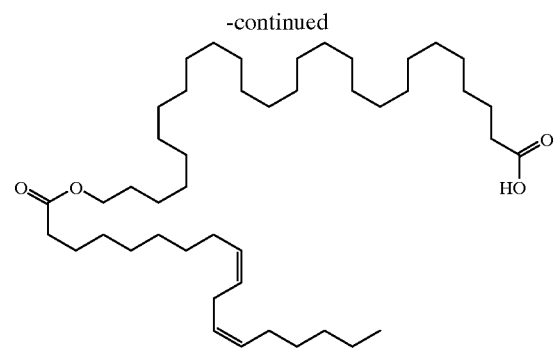

Linoleic acid (100 g; purity 95%, 356 mmoles) was added dropwise over a period of 0.5 hours to a stirred mixture of oxalyl chloride (42 ml; 481 mmoles) and of hexane (120 ml) under nitrogen. After the addition the mixture was refluxed for 1.5 hours and then evaporated under reduced pressure (60° C.; 0.5 mm Hg) to give 107 grams of linoleoyl chloride as an oil.

A mixture of 27-hydroxyheptacosanoic acid (35 g; 82 mmoles), chloroform (500 ml), pyridine (75 ml) and trimethylchlorosilane (9 ml; 71 mmoles) was heated to reflux under nitrogen to give a solution. After refluxing for 0.5 hours the linoleoyl chloride (107 g) was added and the mixture was refluxed for 2 hours.

After cooling water (100 ml) was added and refluxing was continued for 10 minutes. The organic layer was separated, washed twice with 1 N hydrochloric acid (350 ml and 200 ml), dried with sodium sulphate, filtered and evaporated to give an oil. This was crystallised from warm heptane (250 ml) to give a solid. Two more crystallisations from 250 ml of warm heptane yielded 25.34 grams of the title compound.

PMR-spectrum (Bruker; 360 MHz; CDCl$_3$; values in ppm); δ: 0.89 (t, 3H); 1.2–1.6 (m, 64H); 2.05 (m, 2×2H); 2.29 and 2.34 (2×t, 2×2H); 2.77 (t, 2H); 4.0 (t, 2H); 5.35 (m, 4H).

B. The Preparation of N-(27-Linoleoyloxyheptacosanoyl)-phytosphinaosine.

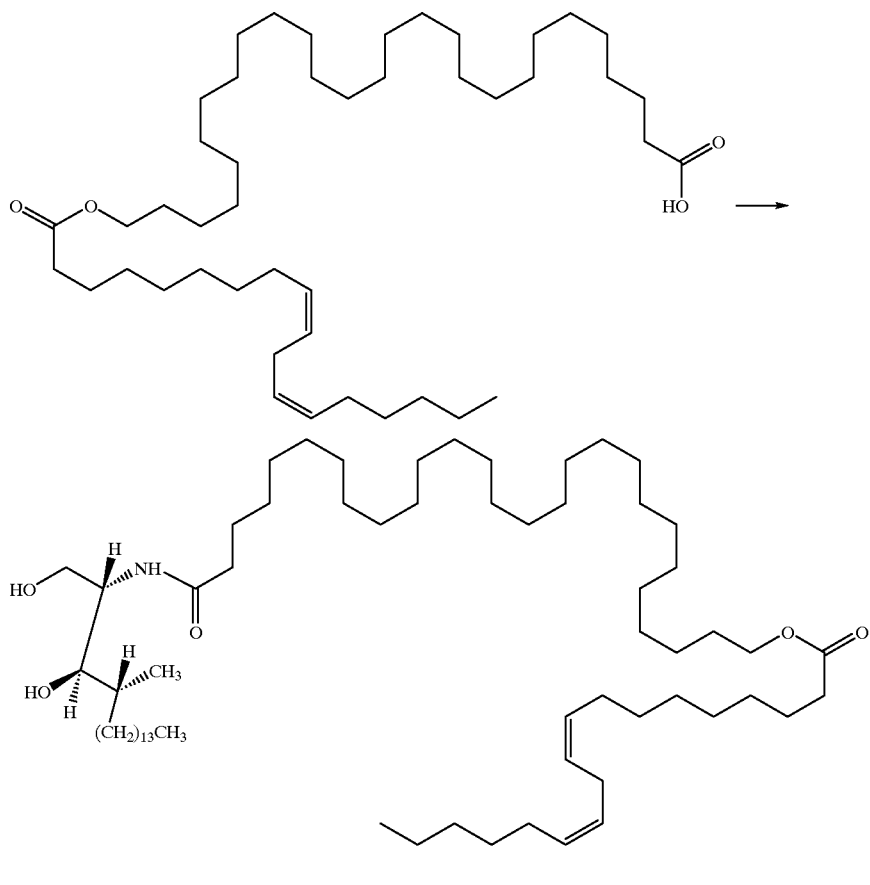

A. Via a Mixed Anhydride

A solution of 27-linoleoyloxyheptacosanoic acid (5 g; 7.2 mmoles) in chloroform (70 ml) and triethyl amine (4 ml, 28.8 mmoles) was added to a stirred solution of p-toluene-sulphonyl chloride (1.25 g, 6.6 mmoles) in chloroform (100 ml) over 15 minutes under nitrogen while keeping the temperature at 50° C. After stirring for 50 minutes at 50° C. phytosphingosine (2 g, 6.3 mmoles) was added and stirring was continued for 2 hours at 50° C.

After cooling the mixture was washed respectively with 50 ml of 1N hydrochloric acid, 50 ml of water and brine. The organic layer was dried with sodium sulphate, filtered and evaporated. The residue was crystallised from warm 2-propanol (100 ml) under nitrogen giving 4.13 gram of the impure title compound.

Purification over 60 grams of silica gel (Flash 30–60 μm) with chloroform/methanol (v/v=9/1 and subsequent crystallisation from 100 ml of hot isopropanol gave 2.82 g of the title compound.

PMR-spectrum (Bruker; 360 MHz; CDCl$_3$); values in ppm; δ: 0.87 (t, 6H); 1.0–2.0 (m, 94H); 2.21 and 2.27 (2×t, 4H); 2.76 (t, 2H); 3.58 (m, 2H); 3.72 and 3.90 (ABq; 2H); 4.04 (t, 2H); 4.13 (m, 1H); 5.35 (m, 4H).

B. Using a Carbodiimide

A mixture of 27-linoleoyloxyheptacosanoic acid (5 g, 7.2 moles), chloroform (90 ml), dried 1-hydroxybenzotriazole (3.2 g, 27.3 mmoles), phytosphingosine (3.07 g, 9.7 mmoles) and N,N'-diisopropylcarbodiimide (2.2 ml, 14.1 mmoles) was stirred under nitrogen for 90 minutes at 45° C. and then overnight at room temperature. After washing with 50 ml of a 1N hydrochloric acid solution and brine and filtration the organic layer was concentrated. After addition of hot isopropanol (150 ml) the mixture was filtered while still hot. After cooling down the precipitate formed was filtered off, washed with isopropanol (30 ml), acetone (10 ml) and dried giving 3.7 g of the title compound.

EXAMPLE 3

The Synthesis of N-(27-oleoyloxyheptacosanoyl)-phytosphingosine

A: The Preparation of 27-oleoyloxyheptacosanoic acid.

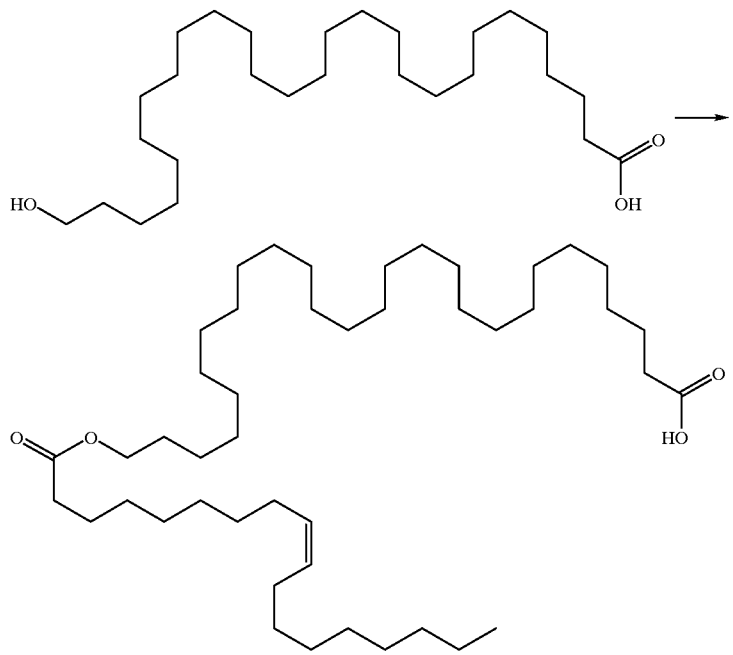

A mixture of 27-hydroxyheptacosanoic acid (10 g, 23 mmoles), chloroform (250 ml), pyridin (25 ml, 309 mmoles) and trimethylsilyl chloride (3.1 ml; 24.4 mmoles) was stirred over 30 minutes at 64° C. Then oleoyl chloride (30 ml) was added, the reaction mixture was refluxed for 2 hours, water (100 ml) was carefully added and refluxing was continued for another 15 minutes.

The organic layer was separated, washed with a 1N hydrochloric acid solution and concentrated. After addition of n-hexane the precipitate formed was filtered off and purified via column chromatography (silica gel (300g); eluens chloroform/methanol: 9/1. Concentration of the appropriate fractions (3–11), treatment with warm heptane (120 ml) gave after cooling, filtration and recrystallizing from hot heptane 8.67 of the title compound.

PMR-spectrum (Bruker; 360 MHz; $CDCl_3$); values in ppm; δ: 0.88 (t, 3H); 1.0–1.6 (m, 70H); 2.00 (m, 2×2H); 2.29 and 2.34 (2×t, 2×2H); 4.06 (t, 2H); 5.34 (m, 2H).

B. The Preparation of N-(27-oleoyloxyheptacosanoyl)-phytosphingosine.

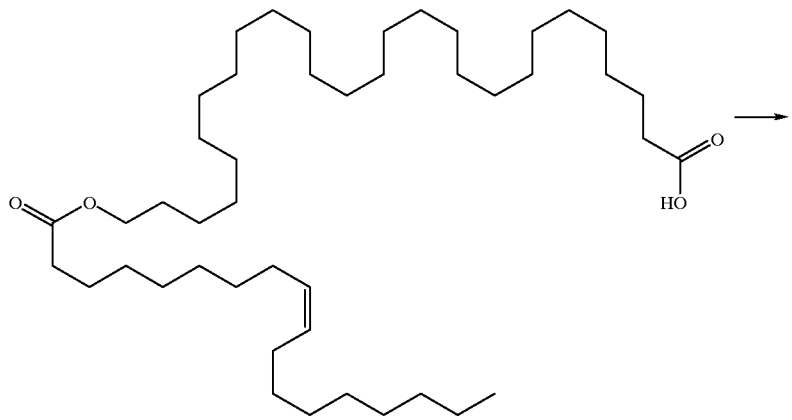

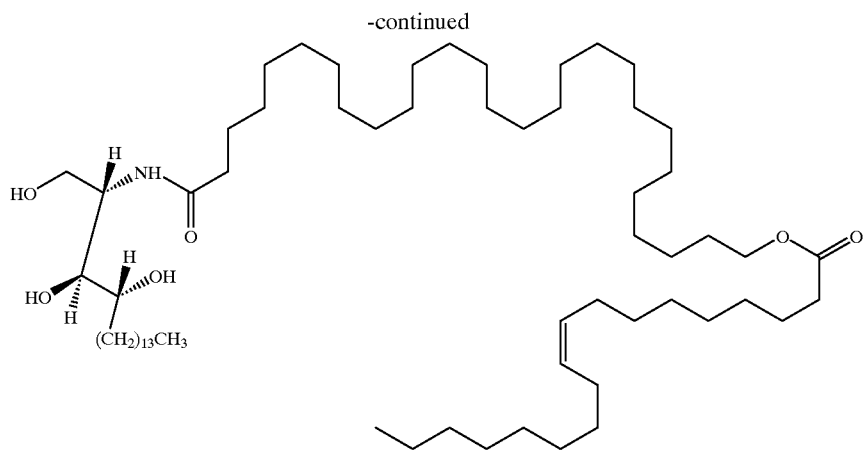

A. Via a Mixed Anhydride

A solution of 27-oleoyloxy-heptacosanoic acid (2 g; 2.89 mmoles) in chloroform (30 ml) and triethylamine (1.6 ml; 11.5 mmoles) was added in 30 minutes to a stirred solution of 0.5 grams of p-toluenesulphonyl chloride (0.5 g; 2.6 mmoles) in chloroform (40 ml) under nitrogen while keeping the temperature at 50° C. After stirring for 1 hour at 50° C. phytosphingosine (0.8 g; 2.52 mmoles) was added and stirring was continued for 2 hours at 50° C. After cooling the mixture was washed with 50 ml of 0.5 N hydrochloric acid, 50 ml of water and brine respectively. The organic layer was evaporated in vacuum and the residue was crystallized from 50 ml of warm 2-propanol under nitrogen giving 2.03 grams of the impure title compound. Purification over 40 grams of silica gel (Flash 30–60 μm) with chloroform/methanol=9/1 and subsequent crystallization from 40 ml of hot isopropanol gave 0.74 g of the title compound.

PMR-spectrum (Bruker; 360 MHz; CDCl$_3$; values in ppm). δ: 0.87 (t, 6H) ; 1.0–2.0 (m, 100H) ; 2.22 and 2.27 (2×t, 4H); 3.58 (m, 2H); 3.73 and 3.90 (dABq, 2H); 4.04 (t, 2H); 4.13 (m, 1H); 5.33 (m, 2H); 6.32 (d, 1H).

B. Using a Carbodiimide

A mixture of 27-oleoyloxyheptacosanoic acid (2 g, 2.9 mmoles), chloroform (76 ml), dried 1-hydroxybenzotriazole (1.28 g, 10.9 mmoles), phytosphingosine (1.23 g, 3.9 mmoles) and N,N'-diisopropylcarbodiimide (0.88 ml, 5.64 mmoles) was stirred under nitrogen for 24 hours at room temperature. After adding 50 ml of a 1N hydrochloric acid solution and stirring the organic layer was filtrated, washed with brine and concentrated. The title product (2.07 g) was obtained by crystallization from hot isopropanol (50 ml).

EXAMPLE 4

The Synthesis of N-(27-hydroxyhentacosanoyl)-phytospingosine

Diisopropylcarbodiimide (1 ml, 6.4 mmoles) was added to a stirred suspension of 27-hydroxy-heptacosanoic acid (2.13 g, 5 mmoles), dry tetrahydrofuran (50 ml), dried 1-hydroxy-benzotriazole (1.6 g, 13.5 mmoles) and phytosphingosine (1.5 g, 4.7 mmoles) at 40° C. under nitrogen. After stirring overnight the mixture was cooled to room temperature and the precipitate was filtered off and washed with 20 ml of tetrahydrofuran.

The filtercake was dissolved in a hot mixture of 300 ml of chloroform and 17 ml of methanol and cooled to room

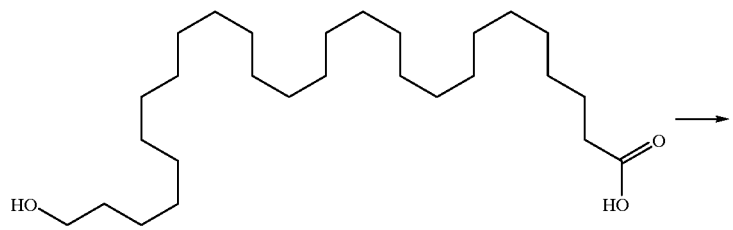

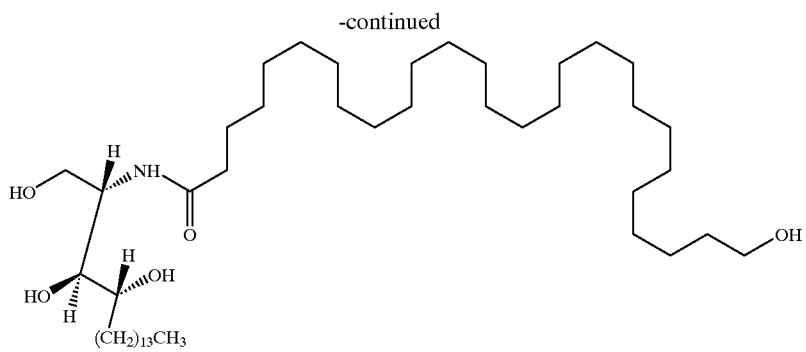

temperature. The precipitate was filtered off, washed with chloroform and with acetone and dried in vacuum at 35° C. to give 2.66 g of the title product.

PMR-spectrum (Bruker; 360 MHz; CDCl$_3$/pyridin-d5, 1/1; 328 K; values in ppm); δ: 0.96 (t, 6H); 1.0–2.1 (m, 74H); 2.32 (t, 2H); 3.79 (t, 2H); 3.9–4.3 (m, 4H); 4.65 (m, 1H); 7.50 (d, 1H).

EXAMPLE 5

The Synthesis of N-(23-stearoyloxy-tricosanoyl)-phytosrhingosine

A. 23-OH-tricosanoic acid Benzyl Ester

A suspension of ca. 117 mmol 23-OH-tricosanoic acid, 250 ml dimethylformamide, 25 ml (210 mmol) benzyl bromide, 250 ml acetone and 25 g anhydrous potassium carbonate is stirred mechanically and brought to reflux (ca. 76° C.) under a N$_2$ atmosphere.

After 3.5 hours at reflux, the suspension is cooled to 40° C. and poured into 1000 ml water under stirring. The precipitate is filtered and washed with water.

The filter cake is warmed in 500 ml toluene on a steam bath until the filter cake is almost dissolved. The mixture is then poured into a 1 l separatory funnel which is prewarmed with steam.

The organic layer is separated and filtered through coarse-grade filter paper. The aqueous layer is extracted with a further 100 ml warm toluene which is in turn used to wash the filter paper.

The toluene fractions are combined and warmed and about 100 ml of the liquid is removed by distillation under atmospheric pressure.

The residue is cooled slowly to room temperature whereby a precipitate forms. The precipitate is filtered, washed with toluene and dried to yield the title compound.

B. 23-stearoyloxy-tricosanoic acid Benzyl Ester 13 ml stearic acid chloride is added to a stirred mixture of ca. 28.2 mmol 27-OH-tricosanoic acid benzyl ester and 100 ml pyridine. The temperature of the solution rises from room temperature to 33° C.

After stirring for 24 hours, 100 ml water is added and the solution is stirred for a further 1 hour.

The precipitate is filtered and washed with water and with approx. 200 ml methanol.

Drying under vacuum gives the raw product, which is then recrystallized from 175 ml ethyl acetate, yielding the title compound.

C. 23-stearoyloxy-tricosanoic acid

The 23-stearoyloxy-tricosanoic acid benzyl ester obtained from the previous step is dissolved in 350 ml alcohol-free methylene chloride and is warmed slightly. 3 g 10% Pd/C catalyst is added and the solution is flushed with N$_2$. The solution is then stirred under H$_2$ for a period of 3 hours.

After flushing with N$_2$, 150 ml ethanol-free chloroform is added and the mixture is warmed to dissolve the organic material.

The Pd/C catalyst is removed by filtration and washed with chloroform.

The chloroform fractions are combined and evaporated until dry providing the title compound.

D. N-(23-stearoyloxy-tricosanoyl)-phytosphingosine

A solution of ca. 1.44 minol 23-stearoyloxy-tricosanoic acid, 50 ml methylene chloride and 2 ml triethylamine is brought to reflux (41° C.). 250 mg (1.31 mmol) p-toluene sulfonyl chloride is added to the refluxing solution.

After 0.5 hours at reflux, 300 mg (ca. 0.9 mmol) phytosphingosine is added and the solution is allowed to reflux for a further 45 minutes.

After cooling to 30° C., the precipitate is filtered and subsequently washed with methylene chloride, acetone and water and dried to give a solid material. This solid is dissolved in 15 ml hot, ethanol-free chloroform and filtered while warm. The filtrate (ca. 20 ml) is allowed to cool. The title compound is crystallized from this filtrate.

EXAMPLE 6

Cream-Base Containing N-(27-stearoyloxy-heptacosanoyl)-phytosphingosine

|    | Ingredient      | Manufacturer      |         |
|----|-----------------|-------------------|---------|
| A. | Title compound  | Present invention | 0.50%   |
|    | Lanette 0       | Henkel            | 8.00%   |
|    | Cremophor A-25  | BASF              | 2.00%   |
|    | White Vaseline  |                   | 10.00%  |
|    | Paraffin liquor |                   | 10.00%  |
| B. | Distilled water |                   | 69.50%  |
|    |                 |                   | 100.00% |

The ingredients of fraction A are mixed and warmed to ca. 80–85° C. Distilled water (fraction B) is warmed to ca. 80–85° C. and added fraction A under thorough mixing, if necessary with an homogenizer. While stirring, the mixture is allowed to return to room temperature.

EXAMPLE 7

Cream-Base Containing N-(23-stearoyloxy-tricosanoyl)-phytosphingosine

This composition is prepared in a manner which is identical to that described in Example 3 except that N-(23-stearoyloxy-tricosanoyl)-phytosphingosine is used in place of N-(27-stearoyloxy-heptacosanoyl)-phytosphingosine.

EXAMPLE 8

All-Puroose Cream Containing N-(27-stearoyloxy-heptacosanoyl)-phytosphinaosine

|    | Ingredient        | Manufacturer      |         |
|----|-------------------|-------------------|---------|
| A. | Title compound    | Present invention | 0.50%   |
|    | Stearic acid      |                   | 10.00%  |
|    | Lanette 0         | Henkel            | 2.00%   |
|    | Eutanol G         | Henkel            | 6.00%   |
|    | Emulgin B1        | Henkel            | 2.00%   |
|    | White bee wax     |                   | 3.00%   |
|    | Paraffin liquor   |                   | 10.00%  |
|    | Anhydrous lanolin |                   | 2.00%   |
|    | White Vaseline    |                   | 15.00%  |
| B. | Triethanol amine  |                   | 0.60%   |
|    | Distilled water   |                   | 48.90%  |
|    |                   |                   | 100.00% |

The ingredients of fraction A are mixed and warmed to ca. 80–85° C. Distilled water (fraction B), is warmed to ca. 80–85° C. and added fraction A under thorough mixing, if necessary with an homogenizer. While stirring, the mixture is allowed to return to room temperature.

EXAMPLE 9

All Purpose Cream Containing N-(23-stearoyloxy-tricosanoyl)-phytosphinaosine This composition is prepared in a manner which is identical to that described in Example 5 except that N-(23-stearoyloxy-tricosanoyl)-phytosphingosine is used in place of N-(27-stearoyloxy-heptacosanoyl)-phytosphingosine.

What is claimed is:

1. A compound of the formula:

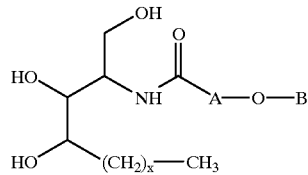

wherein A is $C_{15-35}$ straight chain alkyl group which may optionally contain one or two double bonds, B is a $C_{12-20}$ straight chain acyl group which may optionally contain one or two double bonds and X is 13.

2. The compound of claim 1 wherein A is a $C_{22-31}$ group which may optionally contain one or two double bonds.

3. The compound of claim 1 wherein B is stearoyl, oleoyl or lineoyl.

4. The compound of claim 1 wherein B is lineoyl.

5. The compound of claim 1 wherein said compound is selected from the group consisting of N-(27-stearoyloxy-heptacosanoyl)-phytosphingosine, N-(27-lineoyloxy-heptacosanoyl)-phytosphingosine, N-(27-oleoyloxy-heptacosanoyl)-phytosphingosine, N-(27-lineoyloxy-heptacosanoyl)-phytosphingosine, N-(23-stearoyloxy-tricosanoyl)-phytosphingosine, N-(23-lineoyloxy-tricosanoyl)-phytosphingosine, and N-(23-oleoyloxy-tricosanoyl)-phytosphingosine.

6. The compound of claim 1 prepared from an acyloxy-alkanoic acid of the general formula B—O—A—COOH by chemically coupling to a moiety having the formula $CH_3$—$(CH_2)_X$—$(CHOH)_2$—$CH(CH_2OH)$—$NH_2$ or to an activated acid of said moiety wherein A is $C_{15-35}$ straight chain alkyl group which may optionally contain one or two double bonds, B is a $C_{12-20}$ straight chain acyl group which may optionally contain one or two double bonds and X is 13.

7. The compound of claim 6 wherein said acyloxy-alkanoic acid of the general formula B—O—A—COOH is prepared by a method wherein a $_\omega$-hydroxy alkanoic acid of the formula HO—A—COOH in which the carboxyl group is protected is coupled to an alkanoic acid of the formula B—OH, wherein A is $C_{15-35}$ straight chain alkyl group which may optionally contain one or two double bonds and B is a $C_{12-20}$ straight chain acyl group which may optionally contain one or two double bonds.

8. The compound of claim 7 wherein said $_\omega$-hydroxy alkanoic acid of the formula HO—A—COOH is prepared by a method wherein protected acid chlorides are coupled with enamines prepared from cyclic ketones, followed by ring opening and reduction.

9. A cosmetic composition for topical application comprising from 0.001% to 25% of at least one compound according to claim 1 in a cosmetically acceptable excipient.

10. A pharmaceutical composition for topical application comprising from 0.001% to 25% of at least one compound according to claim 1 in a pharmaceutically acceptable excipient.

11. A method of treating mammalian skin comprising applying a cosmetic composition comprising a compound according to claim 1 to said skin.

12. A method according to claim 11 wherein said composition is used for the restoration of moisture to said mammalian skin.

13. A method of treating mammalian skin comprising applying a pharmaceutical composition comprising a compound according to claim 1.

14. A method according to claim 13 for the treatment of atopic eczema in mammals.

* * * * *